United States Patent [19]

Pomatto et al.

[11] Patent Number: 5,094,229

[45] Date of Patent: Mar. 10, 1992

[54] CRANIAL REMODELING ORTHOSIS

[76] Inventors: Jeanne K. Pomatto; R. Craig Pomatto, both of 24200 N. Alma School Rd., No. 35, Scottsdale, Ariz. 85255

[21] Appl. No.: 653,043

[22] Filed: Feb. 11, 1991

[51] Int. Cl.⁵ ............................ A61F 5/08; A42B 1/06
[52] U.S. Cl. .................................... 602/17; 128/857; 2/410
[58] Field of Search ............... 128/76 R, 845, 846, 128/857; 2/410, 417

[56] References Cited

U.S. PATENT DOCUMENTS

| | | | |
|---|---|---|---|
| 678,417 | 7/1901 | Muller | 128/76 R |
| 2,825,328 | 3/1958 | Olsen | 128/76 R |
| 2,855,202 | 10/1958 | Kinne | 128/76 R X |
| 3,645,259 | 2/1972 | Schulman | 128/857 X |
| 3,834,379 | 9/1974 | Grant | 128/857 |
| 4,352,352 | 10/1982 | Janovsky et al. | 128/76 R |
| 4,645,198 | 2/1987 | Levenston | 128/76 R X |
| 4,646,728 | 3/1987 | Takeda | 128/76 R X |
| 4,735,196 | 4/1988 | Krag et al. | 128/76 R X |
| 4,776,324 | 10/1988 | Clarren | 128/76 R |
| 4,809,690 | 3/1989 | Bouyssi et al. | 128/76 R X |
| 4,854,306 | 8/1989 | Pujals, Jr. | 128/76 R X |
| 4,954,815 | 9/1990 | Delmonte | 128/76 R X |
| 4,982,451 | 1/1991 | Graham | 2/410 |
| 4,986,282 | 1/1991 | Stackhouse et al. | 128/857 |
| 5,003,968 | 4/1991 | Mars | 128/76 R X |
| 5,010,898 | 4/1991 | de Kanawati et al. | 128/845 |

FOREIGN PATENT DOCUMENTS

| | | | |
|---|---|---|---|
| 0280042 | 8/1988 | European Pat. Off. | 2/417 |
| 0009114 | of 1914 | United Kingdom | 128/857 |

OTHER PUBLICATIONS

Clarren, S. K., et al., "Helmet Treatment for Plagiocephaly and Congenital Muscular Torticollis", The Journal of Pediatrics, 94(1):43-46, 1979.

Primary Examiner—Richard J. Apley
Assistant Examiner—Linda C. M. Dvorak
Attorney, Agent, or Firm—Cahill, Sutton & Thomas

[57] ABSTRACT

A cranial remodeling band has an internal surface shaped to the configuration to which a subject's cranium is to be reconfigured. The band has at least one discontinuity therein permitting relative movement of anterior and posterior portions of the band. An elastic member extending across the discontinuity biases the anterior and posterior regions toward each other.

8 Claims, 1 Drawing Sheet

U.S. Patent     Mar. 10, 1992     5,094,229
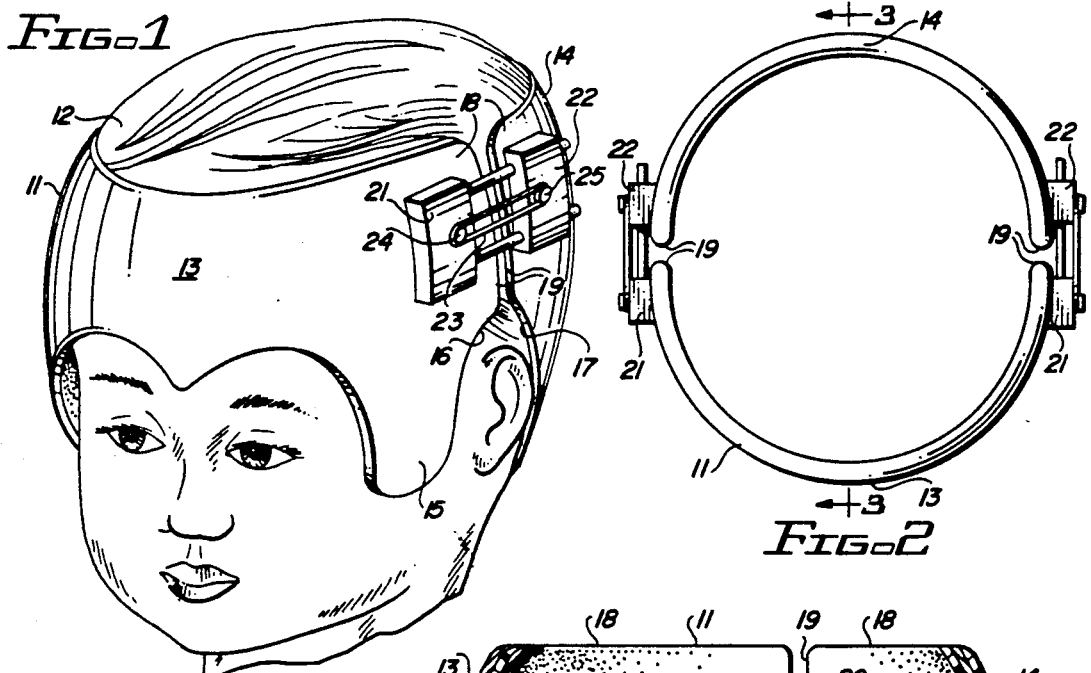
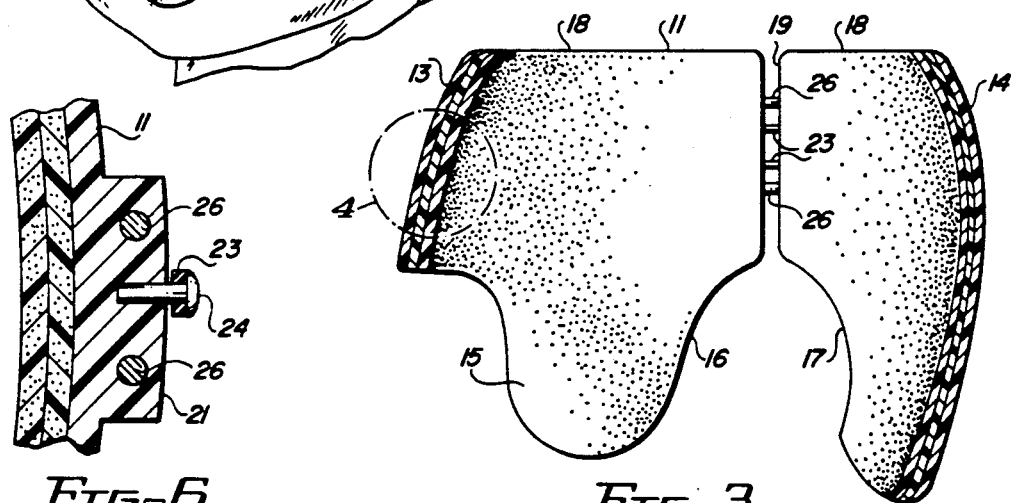
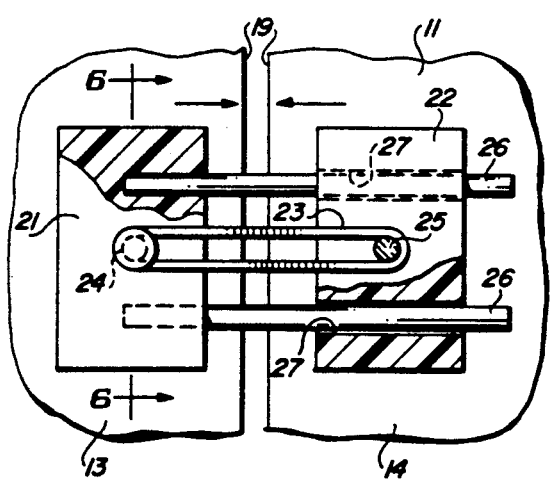
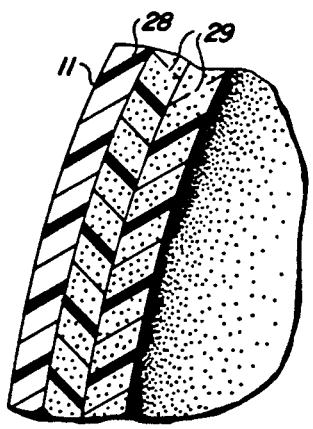

CRANIAL REMODELING ORTHOSIS

TECHNICAL FIELD

This invention is concerned with correcting plagiocephaly, an abnormal head shape possessed by a human.

BACKGROUND ART

Cranial deformities for an otherwise normal child can result from aberrant constraint of the fetal head during late uterine life. Plagiocephaly can also contribute to facial asymmetry.

In some subjects with plagiocephaly, the head will correct its shape over time, but with others the condition may persist as a cosmetic disability. Given the latter possibility, it is desirable to attempt correction of the deformation when the subject is less than a year old and preferably during the first six months of life when the brain and cranium are growing at a rapid rate and the sutures in the cranium have not rigidified.

Researchers in this field have previously discovered that confining the cranium within a specially shaped helmet can result in remodeling the cranium as it expands against the helmet with growth. One such effort has been reported by S. K. Claren, D. W. Smith, and J. W. Hanson in the January 1979 issue of *The Journal of Pediatrics* (Volume 94, No. 1) at Pages 43–46 in an article entitled "Helmet Treatment for Plagiocephaly and Congenital Muscular Torticollis". That article is incorporated herein by reference.

S. K. Claren of the aforementioned research team disclosed what he deemed to be an improved helmet treatment in his U.S. Pat. No. 4,776,324, granted Oct. 11, 1988, for "Therapeutic and Protective Infant Helmets". He proposed the use of a graded series of sized helmets to replace the previously used individualized helmets.

There are a number of short-comings or disadvantages associated with helmet treatment of plagiocephaly. The first of these is the result of the passive nature of the helmet treatment which relies entirely on cranial growth to provide the pressure necessary for remodeling to occur. At any given time, the pressure delivered to the cranium may be sub-optimal, optimal, or excessive, depending on the extent of the subject's cranial growth.

The helmet is quite confining and the virtual absence of air circulation therein can result in excessive sweating with little evaporative cooling. The helmet is uncomfortable.

Furthermore, in order for the helmet to be easily removed and replaced, the cranial entry opening therein must have a circumference at least as great as the largest occipitofrontal circumference of the subject's misshapen cranium. As a consequence, the helmet is relatively ineffective to correct cranial deformation distal to and beneath the apex of the cranial deformity. This same requirement for the configuration of the helmet also dictates that a chin strap must be employed to keep the helmet in place. The chin strap can apply deforming forces to the subject's jawbone and interfere with eating and chewing.

There continues to be a need for an improved orthosis for cranial remodeling.

DISCLOSURE OF THE INVENTION

This invention contemplates employing a band encircling the cranium and covering substantial areas of the frontal and occipital bone regions of the cranium. The band has at least one discontinuity therein permitting relative movement of the anterior and posterior portions of the band. Means are provided for applying a closing force across the discontinuity to draw the anterior and posterior portions of the band toward each other to apply pressure to the cranium. The closing force means are preferably elastic.

BRIEF DESCRIPTION OF THE DRAWINGS

The invention is described in greater detail hereinafter by reference to the accompanying drawings, wherein:

FIG. 1 is a perspective view of the head of an infant wearing the cranial remodeling orthosis of this invention;

FIG. 2 is a top view of the orthosis;

FIG. 3 is a vertical sectional view through the orthosis taken as indicated by line 3—3 in FIG. 2;

FIG. 4 is an enlarged view of the region within circle 4 in FIG. 3;

FIG. 5 is an enlarged view of a guide and biasing structure employed in the orthosis; and FIG. 6 is a vertical sectional view taken as indicated by line 6—6 in FIG. 5.

BEST MODES FOR CARRYING OUT THE INVENTION

The cranial remodeling orthosis of this invention takes the form of a band 11 shaped to encircle the cranium 12 of a subject and cover substantial areas of the frontal and occipital bone regions of the cranium. Band 11 comprises an anterior region, or portion, 13 and a posterior region, or portion, 14.

The anterior portion 13 of band 11 preferably includes a depending portion 15 on either side thereof for at least partially covering the temporal bone regions of the cranium.

It is to be noted that, unlike the prior art treatment helmets referred to above, the anterior and the posterior portions 13 and 14 of the band 11 are trimmed, or shaped, at 16 and 17, respectively, to completely expose the ears of a subject wearing the band. Thus, the discomfort and hearing impairment caused by covering the ears are avoided. Also, unlike the prior art, the upper edge 18 of the band 11 terminates well below the top of the cranium. This configuration of the band 11 leaves exposed a substantial portion of the parietal bone regions of the cranium and the upper portion of the frontal bone region. Such exposure allows normal evaporation of perspiration from the scalp and contributes to the comfort of the subject.

The band 11 is provided with at least one, and preferably two, discontinuities 19 which permit relative movement between the anterior and posterior portions 13 and 14 of the band. These discontinuities 19 preferably are positioned on opposite sides of the band 11 proximal to the ears of the subject.

Means are provided for applying a closing force across each of the discontinuities 19. This closing means may comprise a simple adjustable strap or straps connecting the anterior and posterior portions 13 and 14 of the band. However, the preferred means includes an elastic member for exerting a controlled force biasing the portions 13 and 14 of the band together.

The most preferred means for biasing the portions 13 and 14 of the bands toward each other to exert a controlled pressure on the subject's cranium 12 is illustrated in FIGS. 1, 2, 5, and 6. This means includes a pair of blocks 21 and 22 mounted, respectively, on the anterior and posterior portions 13 and 14 on opposite sides of each discontinuity 19. Resilient biasing is provided by an elastic band 23 stretched between pins 24 and 25 on blocks 21 and 22.

Relative movement of the anterior and posterior portions 13 and 14 of the band 11 is preferably confined to a single degree of motion. This is accomplished by providing one or more guide rods 26 on one of the blocks, say 21, and the guide rods 26 are received in a like number of guide bores 27 in the other block 22. This guide arrangement effectively stabilizes the band portions 13 and 14 with respect to each other while permitting them to move toward and away from each other along a straight line.

The band discontinuities 19 and the associated elastic bands 23 and guide rods 26 provide several improved performance characteristics for the orthosis of this invention.

The first improved performance characteristic of the band 11 is that it can be shaped to apply cranial pressure anywhere it is needed throughout the entire inner surface of the band. Thus, cranial regions needing remodeling but located below and inwardly of the apex, or section of maximum occipitofrontal circumference, can be effectively reshaped. Unlike the helmet, which requires the lower inner circumferences of the helmet to be equal to or greater than the maximum misshapen circumference to permit the helmet to be removed and replaced, the band 11 with a discontinuity 19 can be easily removed by slightly moving the anterior portion 13 away from the posterior portion 14. And the fact that the bottom regions as well as the top region of the band 11 can be made smaller than this maximum occipitofrontal circumference, in effect, surrounding the apex of the cranial prominence, renders the band self-retaining. In other words, no chin strap is required to hold the band 11 in place on the subject's cranium.

Another improved performance characteristic of the band 11 is that it is "active" in the application of corrective forces to the cranium. The elastic band or bands 23 biasing the anterior and posterior portions 13 and 14 of the band toward each other assure continuous and uniform application of corrective forces to the cranium during the entire time the band is in place on the subject's cranium and over time as the brain and cranium grow.

Research reveals that pressure in excess of 24 mm of mercury delivered to the skin over a prolonged period of time can result in injury. Ideally, for maximum corrective effect without injury the band 11 is designed to apply corrective forces in the range of 18 mm to 22 mm of mercury to the cranium. These forces can be selected and adjusted through proper selection of the length and durometer of the elastic band or bands 23. For example, as cranial growth occurs in the anterior-posterior dimension, the anterior and posterior portions 13 and 14 of the band 11 are allowed to drift apart to accommodate this change. Over time, slightly longer elastic bands 23 are progressively utilized to prevent an excessive amount of pressure from being applied to the subject's cranium.

The band 11 is preferably formed of a semi-rigid, thermoformable plastic sheet material, such as copolymer polypropylene. This forms the outer layer 28 of the band and is approximately 3/16" thick. The band 11 is preferably lined with two layers 29 of medium density polyurethane foam cushioning material (see FIG. 4).

For maximum effectiveness, the orthosis of this invention should be individualized for the subject whose plagiocephaly is to be corrected. Cranial deformities of a positional nature are created by various combinations of abnormal pressures to the developing cranium. As such, the resulting deformities are similarly diverse with no two heads exhibiting identical patterns of deformation. To achieve the maximum cosmetic improvement, the band 11 should be fabricated from an impression of the head of the subject to be treated.

The fabrication technique is quite simple. A plaster cast is made of the subject's head and this is then used to create a positive mold duplicating the configuration of the head. This positive mold is then modified by the application of clay or plaster to the flattened areas of the cranium. The layers of cushioning material 29 are draped over the modified positive mold and the plastic sheet layer 28 is then vacuum-formed over that mold. The positive mold is removed from the resulting helmet-like structure which is then trimmed to the configuration illustrated in the drawings and described above.

Experimental results to date indicate that the remodeling band of this invention is capable of performing dynamic orthotic cranioplasty for the effective treatment of plagiocephaly.

What is claimed is:

1. A cranial remodeling orthosis comprising a band encircling substantial areas of the occipital and frontal regions of the cranium of a subject, the inner surface of said band being shaped in the configuration to which the cranium of a subject is to be remodeled, said band having at least one discontinuity therein permitting the relative movement of anterior and posterior portions of the band, guide means extending across said discontinuity for limiting the degree of motion of the anterior and the posterior regions relative to each other, and means extending across the discontinuity for biasing the anterior and posterior regions of the band toward each other.

2. The orthosis of claim 1, further characterized in that said band has at least two discontinuities therein disposed in opposite sides of said band, there are resilient means extending across each of said discontinuities, and there are guide means extending across each of said discontinuities for limiting the degree of motion of the anterior and posterior regions relative to each other.

3. The orthosis of claim 1, further characterized in that said discontinuity is located in a region of the band proximal to the ear of the subject.

4. The orthosis of claim 1, further characterized in that said band has depending extensions thereof covering at least portions of temporal regions of the subject's cranium.

5. The orthosis of claim 2, further characterized in that said discontinuities are located in regions of the band proximal to the ear of the subject.

6. The orthosis of claim 2, further characterized in that the anterior region of the band has depending extensions thereof covering at least portions of the temporal regions of the subject's cranium.

7. A cranial remodeling orthosis comprising a band encircling substantial areas of the occipital and frontal regions of the cranium of a subject, the inner surface of said band being shaped in the configuration to which the cranium of a subject is to be remodeled, said band having at least one discontinuity therein permitting relative movement of anterior and posterior portions of the band, means extending across the discontinuity for biasing the anterior and posterior regions of the band toward each other, and upper and lower regions of the band having internal circumferences which are less than the maximum occipitofrontal circumference of the subject's cranium, whereby the band is self-retaining on the subject's cranium.

8. The orthosis of claim 7, further characterized in that said band has at least two discontinuities therein disposed in opposite sides of said band and there are resilient means extending across each of said discontinuities.

* * * * *